US005726455A

United States Patent [19]
Vurens

[11] Patent Number: 5,726,455
[45] Date of Patent: Mar. 10, 1998

[54] DISK FILM OPTICAL MEASUREMENT SYSTEM

[75] Inventor: Gerard H. Vurens, Fremont, Calif.

[73] Assignee: StorMedia, Inc., Santa Clara, Calif.

[21] Appl. No.: 640,567

[22] Filed: May 1, 1996

Related U.S. Application Data

[60] Provisional application No. 60/000,611, Jun. 30, 1995.
[51] Int. Cl.[6] ............................................. G01N 21/00
[52] U.S. Cl. .......................... 250/559.28; 250/559.27; 250/225; 356/369
[58] Field of Search .................. 250/559.27, 559.28, 250/559.4, 559.45, 225, 228; 356/237, 369

[56] References Cited

U.S. PATENT DOCUMENTS

| | | | |
|---|---|---|---|
| 2,992,588 | 7/1961 | Henderson . | |
| 3,847,024 | 11/1974 | Beever et al. | 73/432 |
| 3,985,447 | 10/1976 | Aspnes | 356/118 |
| 4,129,781 | 12/1978 | Doyle | 250/341 |
| 4,540,281 | 9/1985 | Akiyama | 356/325 |
| 4,626,101 | 12/1986 | Ogawa et al. | 356/237 |
| 4,707,611 | 11/1987 | Southwell | 250/560 |
| 4,745,291 | 5/1988 | Niiya | 250/560 |
| 4,748,329 | 5/1988 | Cielo et al. | 250/559.28 |
| 4,868,383 | 9/1989 | Kurtz et al. | 250/228 |
| 4,873,430 | 10/1989 | Juliana et al. | 250/225 |
| 4,922,200 | 5/1990 | Jackson et al. | 356/369 |
| 4,972,092 | 11/1990 | Schmitt et al. | 250/571 |
| 5,098,195 | 3/1992 | Halyo et al. | 374/9 |
| 5,153,426 | 10/1992 | Konrad et al. | 250/227.24 |
| 5,182,618 | 1/1993 | Heinonen | 356/446 |
| 5,258,363 | 11/1993 | Hed | 505/1 |

OTHER PUBLICATIONS

Chwalow, M.L.E., et al., "Automatic Brewster's Angle Thin Film Thickness Measurement Spectrophotometer," *IBM Technical Disclosure Bulletin*, vol. 20, No. 8, 3133–3134 (Jan. 1978).

Meeks, S., et al., "Optical Surface Analysis of the Head–Disk–Interface of Thin Film Disks," *Transactions of the ASME*, presented Oct. 1994, Maui, Hawaii.

*Primary Examiner*—Edward P. Westin
*Assistant Examiner*—Kevin Pyo
*Attorney, Agent, or Firm*—Lahive & Cockfield, LLP

[57] ABSTRACT

A method and apparatus for inspecting a reflective surface, or material on such surface, such as lubricant and planarizing layers on a magnetic media storage disk. A beam of controlled polarization impinges obliquely at a spot in the plane of the disk. A collector such as an integrating sphere is spaced away from the disk and has an opening oriented to catch the oblique specular reflectance from the surface. Preferably the opening is substantially larger than the beam, so that disk run out does not send the beam astray or defeat its measurement, and the oblique beam is aimed at an angle lying between the Brewster angle of the lubricant and that of the adjacent layer. A temperature-controlled laser diode with constant-current driver provides a beam that is free of wavelength hops and amplitude changes, making beam aiming repeatable and allowing point-by-point comparisons of the detected reflectance. The disk spins at high speeds on an encoded shaft, and the assembly is radially stepped to allow inspection of the disk at radial and angular positions while a microprocessor synchronized with the spinning disk collects light data to compile a map of surface reflectance. The polarization may be controlled to enhance image quality for different coatings and improve signal discrimination. Simple logic applied to point-by-point inequalities identifies the nature of physical changes responsible for observed effects. Polarization contrast and time difference contrast images allow visualization of defects and changes in substantially transparent layers well under a quarter wave thickness.

20 Claims, 2 Drawing Sheets

DISK FILM OPTICAL MEASUREMENT SYSTEM

REFERENCE TO RELATED APPLICATION

This application is related to and claims the priority under 35 U.S.C. §119(e) of applicant's U.S. provisional patent application 60/000,611 filed on Jun. 30, 1995.

BACKGROUND OF THE INVENTION

The present invention relates to measurements of light-transmissive thin films or layers of such films, and to measurements of surface topography or detection of surface defects. It specifically relates to optical measurement or detection, and to apparatus for performing such optical measurement or detection of a thin film.

A number of common articles of manufacture now have constructions involving thin films formed on relatively large area smooth substrates, and substrates wherein the underlying surface is reflective, possibly conductive, and at least visually smooth if not optically flat. To develop manufacturing processes for reliably fabricating these articles and to inspect them or understand the defects which arise in these articles, it is necessary to observe the thin films. These films may be liquid or solid, have a thickness substantially under one wavelength of the observation illumination, and may possess features or defects which are observable only with meticulous methodology against the highly reflective substrate, requiring a special probe. To detect changes occurring on such a thin surface coating is an even more challenging task.

In part, sensitivity of a probe is determined by devising a standard against which its measurements can be compared. Thus, for example, U.S. Pat. No. 4,873,430 describes a technique for measuring a thin film or surface effect in which all reflected light is collected by a nearly-contacting detector, and in which a certain degree of signal normalization is achieved using separate detectors for specular and diffuse light collection. A similar device has also been described in a paper of Meeks, Weresin and Rosen presented at the ASM/STLE Tribology Conference, Maui, Hi. in Oct. 15-19, 1994. That system employs an integrating sphere substantially contiguous with and tangent to a disk to capture all diffuse reflection from the disk surface; apertures through the sphere allow two light paths to be directed at the tangent point for illumination of the point at 60° incidence and collection of the specular component reflected from that point. The device includes automated scanning and collection, and autocalibration is achieved using reference mirrors.

While each of these approaches utilizes sound theoretical models to address the problem of obtaining normalizable and meaningful levels of signal from a thin film, many practical realities should be recognized in the operation of these devices. Thus, for example, the taking of reflectance measurements on a micrometer-scale region may require multiply-repeated sampling and averaging, or integrating, to obtain a repeatable result. Furthermore, while it may be considerably more informative to compare like measurements taken from many consecutive points on a single disk, even the collection of many thousands of data samples may still provide relatively sparse information about the total working surface of the disk. Furthermore, one of the more interesting avenues of research, involving wear test measurements taken from the same disk before and after use, is severely hampered by the difficulty or impossibility of achieving submicron registration of the disk with an earlier position once it has been removed from the measurement stage. This restricts such tests to the brief wear testing that can be performed while the disk remains on the optical measurement stage, or to relatively uninformative comparison of measurement ensembles, rather than pointwise measurement comparisons taken on a single disk over an extended time.

Accordingly, improvements in optical film measurement apparatus are desirable.

SUMMARY OF THE INVENTION

Various problems described above are addressed and measurements of thin lubricant and protective film layers on a disk surface are reliably achieved in an apparatus and method for measurement of surface coating on a storage medium disk, comprising a disk support stage which independently rotates the disk while a probe support translates linearly with respect to the disk orthogonally of the rotation axis. A collimated, polarized light source provides a beam of polarized light angularly-directed at a point in the plane of disk rotation, and a light collector, such as an integrating sphere with an input aperture larger than the width of the beam and tilted with respect to the plane of rotation, collects light from the illuminated point. The light collector is positioned away from the disk to fully receiving the beam specularly reflected from the disk and to detect the amount of polarized light so received, from which it determines a property of the fill layer. Properties measured by the device include thickness profile of the layer, change of thickness or uniformity thereof, surface roughness, and degradation or optical change of the layer material. The beam has a spot size under about ten micrometers, and is directed at one or more layers each of which is substantially under one micrometer thick. In one embodiment, the source includes a laser diode which is temperature stabilized to emit laser light at a single wavelength, and the diode is driven by a current-controlled signal to produce a beam with substantially constant amplitude. This beam is shaped, collimated and polarized to illuminate a circumferentially elongated spot on the disk. The collector is positioned with its collection aperture approximately one to five centimeters away from the disk, and is oriented to receive substantially only light that is specularly reflected from the disk. A wavelength or polarization filter may be positioned in front of the collector to partially shield the detector output from ambient light and enhance the extinction ratio.

In this embodiment, temperature stabilization of the laser removes wavelength-dependent steering jumps in the optical path, while stabilization of the diode electrical drive current removes background amplitude changes, allowing detection of reflectance or absorbance changes as low as 0.01 percent without requiring time-consuming processes such as averaging of multiple readings or performing lengthy integrations. The method and apparatus produce fast and highly accurate surface reflectance maps of the disk coating in radial coordinate R, disk rotation angle $\theta$ and polarization angle $\phi$.

In a preferred embodiment, the device performs measurements on the surface of a magnetic disk having a body and a multilayer structure set up to define magnetic storage domains in a thin subsurface magnetic storage layer. A surface lubricant layer coats the top, and a protective carbon planarizing layer lies below the lubricant, between the magnetic storage layer and the surface lubricant layer. The input illumination is directed at an angle which lies between Brewster's angle of the lubricant and that of the carbon layer, and a processor controls the polarizer, and a computer receives coordinating signals from the disk drive and the probe transport to synchronize acquisition, i.e., to digitize and store detected light values as the stage moves through an array of disk positions, thus compiling a map of disk reflectance at one or more polarizations. In one embodiment a laser source is maintained at a substantially constant temperature by a Peltier device and is driven to produce a constant output intensity. The entire assembly operates stably over a temperature range of at least 0 to 50° C., and is insensitive to humidity so long as thermal cycling is conducted in such a way that condensation does not occur. The apparatus operates in an environmental test chamber, and a disk may remain on the test stage and be measured before, after and even during environmental testing. Comparison of the coordinates of a first acquired reflectance data map with a later acquired one resolves changes in thickness due to wear, evaporation or material redistribution. A simple logic table may indicate the nature of physical process responsible for evolving reflectances changes.

BRIEF DESCRIPTION OF DRAWINGS

These and other features of the invention will be understood from the disclosure and claims presented herewith, together with the illustrative drawings showing details of a representative embodiment, wherein

DETAILED DESCRIPTION

Figure 1:
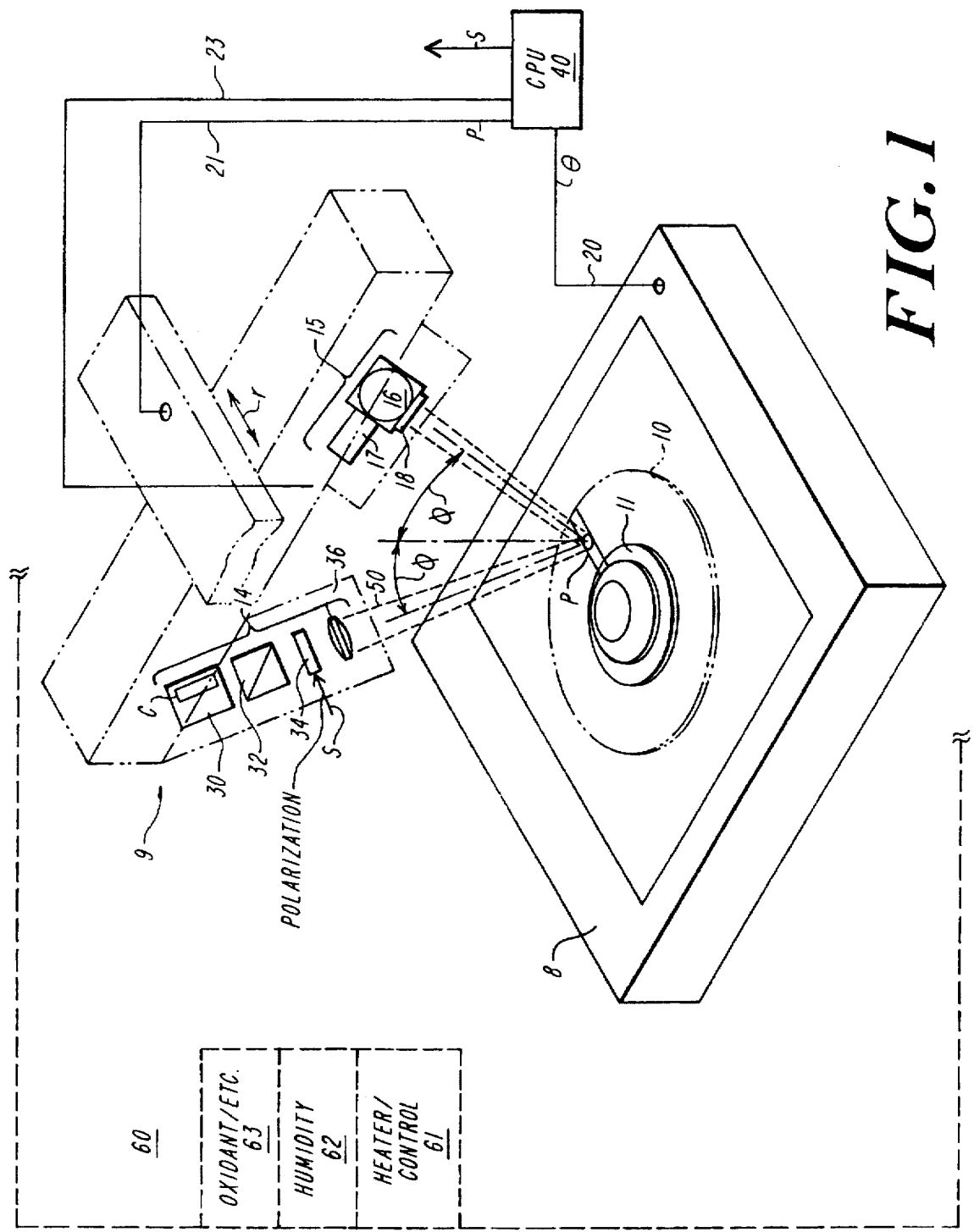
FIG. 1 shows a disk film optical measurement system in accordance with the present invention.

FIG. 1 illustrates a prototype embodiment 100 of the present invention, which includes a test stand or base 8 for holding a disk to be tested, and an optical measurement assembly 9 which is movably suspended on a track or stage for one-dimensional translational movement along axis r over the base 8. Base 8 includes a motor driven turntable 11, e.g., a conventional so-called hard disk drive for rotating a magnetic media storage disk 10, (shown in phantom) as well as a magnetic head and carrier of conventional type (not shown) for reading information from and writing information onto the disk 10. Turntable 11 turns on a shaft (not shown) which has a 1024 position shaft encoder, and corresponding angular position signals corresponding to a shaft rotation angle $s_\theta$ appear on line 20, which connects via appropriate circuitry to synchronize measurement acquisition in a processor, CPU 40. The position signals include a zero-position synchronization or framing signal, followed by the $2^{10}$ encoder signals in each rotation. The turntable may, for example, turn at 3,600 or 5,400 RPM, corresponding to sixty or ninety thousand shaft encoder positions per second; if measurement speed is critical, a faster motor, a more finely divided shaft encoder, and/or special control chips may be used to interpolate sample positions or otherwise increase the number of data points per second.

Above the turntable 11, the movable optical measurement assembly 9 is mounted so that an illumination assembly 14 and a detection assembly 15 are positioned and aligned symmetrically about a probe a point P in the plane of disk 10. Movement of the assembly stage 9 scans the point P radially across the disk. Stage 9 is stepper controlled in one micrometer increments, and position indicating and control signals are continuously monitored or controlled by CPU 40 on line 21, to synchronize or coordinate the r, θ positions illuminated on the disk 10 with optical results from the optical measurement assembly 14, 15, which are provided to CPU 40, after suitable conditioning, along line 23.

In one embodiment of the optical measurement assembly 14, 15, the illumination assembly 14 includes a laser source 30 such as a four milliwatt Melles Griot 56DOL603 laser diode source producing a 670 nm output beam and an objective optical assembly 36 which focuses the laser beam to a small spot on the disk 10. Preferably, a polarization beam splitter 32 and a half-wave plate 34 are placed between the laser 30 (which produces a polarized output beam) and the objective assembly 36, to clean up and more precisely control the polarization state of the illumination beam. The polarizer 32 passes light of a defined polarization, while half wave plate 34 rotates the direction of polarization. Element 34 is a liquid crystal active half wave retarder, which may, for example, be controlled by the CPU, which provides a state control signal on line S so that the illumination assembly automatically provides either a selected s- or p-polarization state. The objective assembly 36 may be a simple but high quality, e.g., diffraction limited; focusing assembly, such as Melles Griot 06 GLC005, with a focal length of 48 mm. This produces approximately a six micron spot size from the laser diode output at the surface of the disk 10.

With the above laser source, the output beam is non-circular, e.g., about two by six millimeters, and the optics reduce the beam to about six by twelve microns at focus. The source is positioned so the long dimension of beam cross-section is aligned circumferentially on the disk. With illumination at 60° incidence, a circumferential extent of about fifteen microns is realized. As noted above, the stage 9 moves in one micrometer increments, so with this spot size the radial sampling dimensions overlap to assure full coverage by spots, of a disk in the radial direction. On the other hand, for a ninety-five millimeter disk, a 1024-position shaft encoder corresponds to a circumferential sampling distance of several hundred micrometers, so that even with the asymmetric beam section there is relatively sparse sampling in the circumferential direction. As noted above, when full area imaging is desired, the data handling, positioning stage and/or software interpolation/timing aspects are modified for greater resolution and speed. In a preferred embodiment, the clock defined by the 1024 mark shaft encoder is tied to a phase locked loop with a five-stage frequency doubler so the angular position output signal is frequency-doubled five times, providing a sample drive clock trigger at thirty-two times the encoder pulse frequency, i.e. $2^{15}$ pulses per revolution. This sampling frequency provides full coverage of the entire disk, at the probe dot size-resolution, in both radial as well as circumferential directions.

Within the laser assembly 30 a temperature sensor which is integral with or contiguous to the laser diode is used to develop control signals for a solid state Peltier effect cooler C that is energized to maintain the laser cavity of the laser diode at a fixed temperature. This prevents the laser output from jumping between cavity modes as the laser operates. The laser is also operated at a constant output level. Such output control may be achieved in several ways. For example, a beam splitter, which also may be formed integrally with the laser diode (such as by providing a partially transmissive, e.g., 0.01% transmissive, back face of the diode cavity) may provide a fixed portion of the output beam energy to a photodetector to develop in a amplitude signal, which is fed in a negative feedback loop to the laser current drive, thus producing a constant amplitude laser output.

Alternatively, rather than sensing and controlling laser output, a simple constant-current driver may be used. In this case a simple current feedback circuit stabilizes the drive signal level. With these two temperature and output stabilizing controls, the laser 30 produces a fixed wavelength output beam, with an amplitude that is constant to within one part in $10^4$.

The detection assembly 15 is mounted on the same stage or carriage as laser 30, and is positioned at an equal angle of incidence over the radial path to receive the light beam specularly reflected from the point P on the disk as the carriage 9 moves along the direction r.

In a prototype embodiment, the collector assembly includes a small (e.g., one inch diameter) integrating sphere 16 having a one quarter inch aperture, with the aperture directed toward the sample position point P and spaced about four centimeters therefrom. A baffled passage or other light shield may be used to shield the collector from light other than that of the reflected beam, and for some protocols a fixed or variable polarizer may be used to selectively pass a particular state of polarization, or a narrow bandpass interference filter may be used to provide further discrimination of light collected by the sphere 16. These elements are indicated by element 18 at the collection aperture. A photodetector 17 is mounted onto the sphere to detect the level of collected light entering the sphere.

The integrating sphere 16 operates to smooth the amplitude of collected light over a dispersed area, so that the entire photoactive area of the photodetector 17 receives collected light and any localized physical variations in the detector do not introduce variations in the detector output. This is especially important since runout of the rotating disk can cause the reflected beam to flit around to different points on a detector unless the light is first smoothed by the integrating sphere. A diffuser may be substituted for the sphere.

Within the sphere a baffle (not shown) preferably shields the detector 17 from receiving direct illumination through the collection aperture. Detector 17 is located at 90° to the light collection inlet, so a relatively small baffle may entirely shield the detector from direct light without significantly reducing the level of internally-reflected collected light.

Thus, the detector 17 at each point in time produces an output indicative of the intensity of light reflected from point P.

The magnetic disk to be sampled may be of a standard commercial size, e.g., about sixty-five or ninety-five millimeters in diameter, and by way of example, may be formed of glass or of an aluminum/magnesium material about 1.9 mm thick. On the surface of a representative disk substrate are deposited a 10–15 micrometer thick nickel-phosphorous layer, followed by a layer of chromium about one thousand Angstroms thick. The actual magnetic storage layer is then laid down as a 500 Angstrom thick layer of a cobalt/platinum/chrome magnetic alloy medium. These layers form a totally reflective top of the disk.

A planarizing layer of carbon about 175 Angstroms thick is then deposited over the magnetic storage layer, and a layer of lubricant, such as a perfluoropolyether with a thickness of about twenty Angstroms, is applied over the carbon layer. The disk itself is highly polished, and typically a narrow band of slightly roughened surface texture is provided at a radially inward position to serve as a parking track on which the magnetic head may be brought to rest when not in use. The roughened texture of the parking track prevents the head from contact-bonding or sticking to the lubricant when the disk is stopped.

A representative cycle of operation of the device proceeds as follows. Initially, the half-wave plate 34 is set to a default or unactuated polarizing state (s- or p-) to provide a light beam 50 having a polarization state $P_1$ at a level determined by the laser diode output and polarizer 32. As the turntable 11 rotates, the optical assembly 9 is moved radially to step through the radial extent of the disk, and the CPU stores digitized representations of the collected beam power for each point specified by coordinates (r, θ) on the disk where $0 \leq \theta < 2\pi$ and $r_{min} < r < r_{max}$, where $r_{mnin}$ and $r_{max}$ are the effective inner and outer diameters of the magnetic disk, for example from the parking track described above to a band a few millimeters in from the circumference. This data collection provides a quantitative record or map of reflectance of all points on the disk for the given polarization state. The half-wave plate may then be energized to change the polarization of beam 50 and compile a similar map at the same (r, θ) positions, with a different polarization. In the prototype embodiments, half-wave plate 34 is a liquid crystal plate, which is actuated with a 0–5 volt signal to toggle between s- and p-polarizations.

The apparatus preferably resides within a closed environmental test chamber 60, provided with heaters and temperature control system 61, together with suitable means for forming or connecting to sources 62, 63 of humidity, oxidant or other environmental agents which may be selectively actuated to expose the disk surface to a variety of environmental test conditions. During such exposure, the disk drive is operated in its normal fashion, and a magnetic head is carried across the face of the disk over the lubricant layer, so various effects such as frictional wear, lubricant erosion or redistribution, and the like occur.

In a further representative protocol, following operation under the test conditions, a second set of reflectance measurements are made to compile a second map, or a comparative reflectance map, of the same disk. During all this time, the disk preferably remains on the turntable so that there is an exact correspondence between the points with fixed (r, θ) coordinate in each data set stored by the CPU 40.

Thus, if surface reflectance maps are made with s- and p-polarizations both before and after testing, one has available information on both the changes in s- and p-polarization reflectance, and the relative mounts of s- and p-polarization reflection at each time.

As noted above, the beam 50 is directed at an angle φ of about 60°, and generally between about 53° and roughly 70°, so that tan (φ) lies between the index of refraction of the lubricant and that of the carbon layer. By operating in a region where the light strikes above the Brewster's angle of one material (e.g., the lubricant) while being below the Brewster's angle for the other (the carbon layer) light of both polarizations will be represented in the collected light. Moreover, the relative amounts of detected s- and p-illumination, and the direction of change in intensity between two measurements can reveal the nature of changes in a simple logical array.

In general, the wavelength of the laser is not very important, since the lubricant film absorbs very little of the light at many available wavelengths, while the carbon film does absorb, but with a typical sensitivity which may be about 0.04% intensity change per Angstrom of film thickness. By stabilizing the laser source as described above, applicant is able to repeatably detect such small changes in amplitude. The temperature stabilization not only enhances the intensity stability, but further assures that beam 50 remains relatively free of mode hopping, so that diffractive jumps do not affect the aim; thus the (r, θ) coordinates taken at two different times will represent the same point P on the disk. The resolution of the reflectance map will in general depend on the spot size of the lens and the accuracy of the encoder used to determine the location on the disk.

The above apparatus has the great advantage of being quantitatively accurate, and of having a "perfect memory" of disk coordinates when the disk remains on the spindle. Typically about seventy per cent of the s-polarized light is reflected, while less than half of the p-polarized light is reflected. Operating against a substantially perfectly reflective background, the total variation of intensity of the reflected light beam due to effects such as scattering, carbon thickness, and texture variation and absorbance is only about two percent. However, with the aforesaid apparatus, variations of 0.1% are readily detected, and the reflectance range is readily expanded to enhance image contrast. The coordinate/intensity map has therefore been found to be quite useful. For example, a very high resolution map of lubricant thickness is obtained by mapping the surface, rinsing the lubricant off, and then compiling a second reflectance map and comparing the two maps pointwise. The CPU 40 may include software modules to determine a pointwise difference map, to expand the range of detected intensity changes and to print out a graphic image of the disk. It may also include pattern detection software to detect and to annotate specific features.

In addition, various enhanced measurement protocols may be implemented with the basic embodiment described above.

Figure 2A:
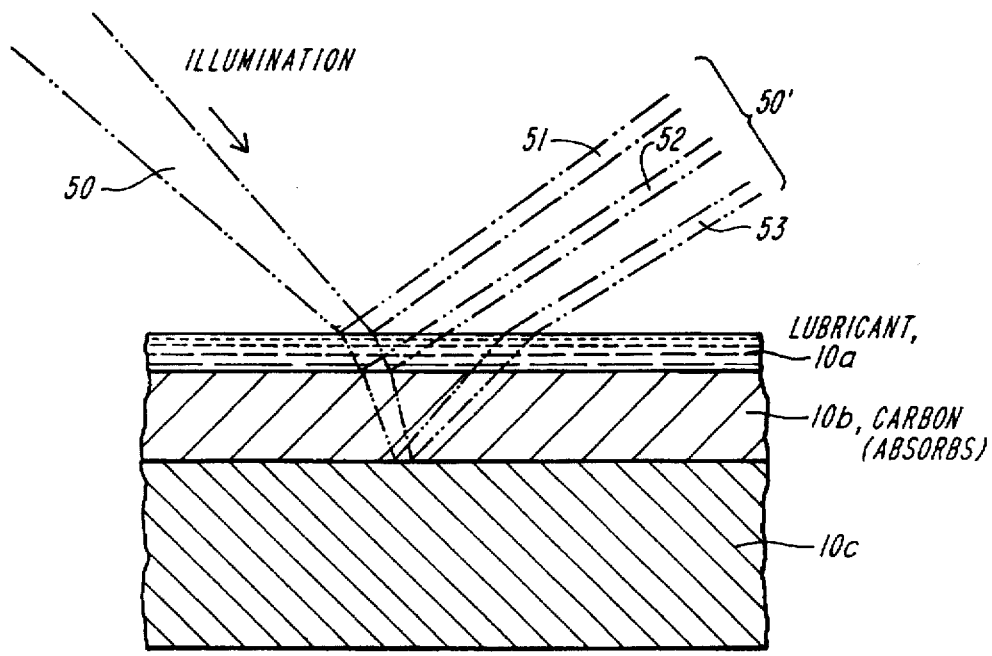
FIG. 2A illustrates polarization and reflection events in the system of FIG. 1.

FIG. 2A illustrates representative polarization-dependent beam effects in the context of a carbon/lubricant two-layer magnetic disk coating system. The top layer 10a of lubricant is only slightly absorptive, but is a dielectric and reflects a substantial portion of one polarization at the given beam angle. The carbon layer 10b on the other hand is absorptive, and absorbs up to about five to eight percent of light traversing that layer and reflected back off the underlying metallic layers 10c. The collected beam 50' includes component beams 51, 52, 53 from the various film surfaces that are enriched in one polarization state (beam 51) or depleted in amplitude (beam 53) or polarization state (beams 52, 53), as will be understood by those skilled in the art. The provision of polarization dependent reflectance maps greatly enhances the ability to probe the state of such coating layers.

Figure 3:
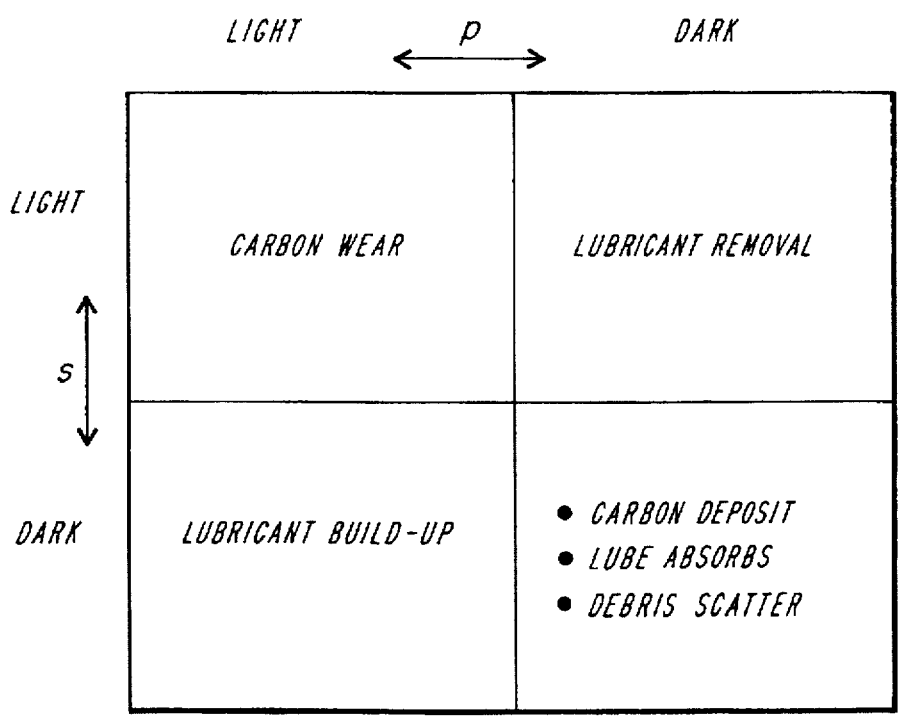
FIG. 3 shows a logic table for identifying physical changes form reflectance changes.

The directional nature of the changes in s- and p-reflectance, and the absorbance of the light of the beam component 53 reflected from the underlying magnetic/metalized substrate 10c allow the small reflectance changes occurring in the reflectance map to be interpreted in terms of physical processes or effects in the observed films. For example, by inspecting one radial track that has been wear tested and then observed in s- and p-light, a simple threshold discrimination between "light" and "dark" may be made either visually or by quantitative comparison to the recorded values in surrounding areas. FIG. 3 illustrates likely physical effects which in theory correspond to the four possible combinations of relative s- and p-image intensity.

As shown in the chart of FIG. 3, a track light in both s- and p-observation beams, corresponds to carbon wear. If light in s- but dark in p-, then there is lubricant removal. An image dark in s- and light in p-corresponds to a condition of lubricant build-up. Finally, if the observed band appears dark in both polarizations, this may correspond to a number of changes, such as deposition of carbon, lubricant degradation and increased absorption, or the presence of scattering debris. Other interpretive meanings will be associated with particular disk images as disk images are compiled and recognizable patterns emerge.

In addition to comparison of two polarization reflectance maps, before and after maps may be subtracted or processed to detect differences, as briefly described above. Furthermore, the apparatus may be used at earlier stages of the disk manufacture to map reflectivity of one or more of the lower coatings on the disk surface. For example, when the disk is metalized with a layer of nickel and polished, the surface may be reflectance mapped to identify each imperfection. These imperfections may then be correlated with features in the later magnetic coating layer or with magnetic signal anomalies measured in the finished disk, to clarify the understanding of media variations and defects or defect-causing traits.

The reflectance maps may also be used to characterize or adjust manufacturing process steps. For example, inspection of the parking track PT or measurement of the width of the transition zone between the track PT and the smoother recording surface may be used to adjust fabrication procedures used to form the roughened PT track, or to identify spill-over effects that may impair performance. The performance variation of different lubricants may also be readily observed, allowing quick evaluation of potential manufacturing materials.

The prototype embodiments described above utilized a 1024 position shaft encoder phase-locked to a frequency multiplier circuit for providing the desired degree of resolution in the circumferential direction, with a stepper-driven motor to carry the rigidly coupled optical illumination and collection assembly over the disk such that the illumination spot follows a radial path across the surface of the disk. The stepper was driven in increments of one micron, which was smaller than the illumination spot. However, the stepper could be actuated in increments of as little as one twenty-fifth of a micron, and the invention further contemplates such actuation in steps below one micron, when using, for example, a smaller illumination spot, or when carrying out specialized protocols such as higher resolution mapping of microdefects, or exploring problems of image alignment or signal variation such as when correlating image maps.

In general, for taking differential aging images, i.e., "before" and "after" data sets of a disk, it is preferred to collect a dense data set of substantially all r, θ, positions so that the corresponding points of each image are readily identified. However, when a point-by-point quantitative comparison is not necessary, it is possible to compile a map of the disk surface at least an order of magnitude faster by running the radial stepper motor and rotational drive motors simultaneously and collecting the reflection data along a spiraling path over the disk surface. This produces a high quality visual image of the entire surface while sampling only a portion of its area. The spiral track data may be acquired in less than a minute, and may be used to quickly assess or survey the disc surface for a trait of interest, such as defect count or a regional pattern of wear or build-up.

Furthermore, while the acquisition of comparative measurements has been described with reference to a turntable 11 having the disk 10 affixed thereto during at least two measurement cycles, the invention also contemplates systems and protocols wherein the disk is removed from the mintable and is then later returned for a subsequent measurement. In that case, to compensate for the de-centering and rotational shift which occur between measurements, the CPU 40 (or a separate image analyzing processor) may include software for correlating two sets of collected data point observations, and determining a corresponding transformation between data sets to allow a differencing or comparison operation to be performed on the two sets on a pointwise basis. Since the disk itself is rigid, once signal correlation has identified the differences in disk position on the turntable, a simple transformation may be used to map one data set to the other and allow pointwise data comparison and to carry out image enhancement operations.

Thus, it will be seen that by providing a specific light source and collecting specular reflection remote from the disk, and by smoothing the collected light before detection away from the surface, a highly informative signal is obtained for evaluation of multiple layers of a reflective surface. The invention being thus disclosed in respect of a representative embodiment, and measurement techniques being described for representative surface layers, further variations and modifications will occur to those skilled in the art, and these are understood to be within the spirit and scope of the present invention and its equivalents, as defined by the claims appended hereto.

What is claimed is:

1. A method of evaluating at least one of lubricant coating thickness and coating wear on magnetic media disks subject to variable environmental and test conditions, such method comprising:

A) providing a magnetic media disk including
      i) a magnetic media layer,
      ii) a coating layer overlying said magnetic media layer, and
      iii) a lubricant layer overlying said coating layer;
   B) supporting said magnetic media disk for rotation about a central axis extending normal to the substrate plane of said disk, and positioned for relative translation orthogonally of said axis with respect to a light source, said supporting being operable to selectively rotate said magnetic media disk about said axis as illumination is independently translated on said rotating disk orthogonally of said axis;
   C) generating a collimated light beam with the light source displaced from said magnetic media disk;
   D) polarizing said collimated light beam emanating from said light source to provide polarized light;
   E) providing position indicating means operable to determine a particular location on said disk upon which said polarized light impinges;
   F) providing an integrating sphere displaced from said disk upon which said polarized light impinges, said integrating sphere having
      i) a light receiving aperture having an axis inclined relative to said plane of said disk and a width larger than width of said light beam so as to be operable to fully receive said beam from diverse, radially displaced light beam impingement locations on said disk, said aperture being generally axially intersected by the specular polarized light reflected from said disk, and
      ii) light intensity measuring means defined by at least a portion of the interior of said integrating sphere;
   G) in a measurement with respect to said particular location on said disk, directing said polarized light against said disk at said particular location and, during said measurement,
      i) reflecting said polarized light from said particular disk location, through said light receiving aperture of said integrating sphere, and into the interior of said integrating sphere, and
      ii) measuring the amplitude of said polarized light impinging upon the interior of said integrating sphere during said measurement, and
   H) determining at least one of wear of said coating layer and change in lubricant layer thickness at said particular disk location at least partially in response to said amplitude measurement.

2. A method of evaluating in at least one of lubricant coating thickness and coating wear on magnetic media disks subject to variable environmental and test conditions, such method comprising:

A) providing a magnetic media disk including
      i) a magnetic media layer,
      ii) a coating layer overlying said magnetic media layer, and
      iii) a lubricant layer overlying said coating layer;
   B) supporting said magnetic media disk for rotation about a central axis extending normal to the substrate plane of said disk, and positioned for relative translation orthogonally of said axis with respect to a light source, said supporting being operable to selectively rotate said magnetic media disk about said axis as illumination is independently translated on said rotating disk orthogonally of said axis;
   C) generating a collimated light beam with the light source displaced from said magnetic media disk;
   D) in response to changes in environmental temperature, modifying the temperature of said light source to maintain a generally constant temperature thereof and, operating at said generally constant temperature, stabilizing said light source to
      i) maintain a constant intensity of light in said collimated light beam; and
      ii) maintain a constant wavelength of light in said collimated light beam;
   E) polarizing said collimated light beam emanating from said temperature stabilized light source to provide polarized light;
   F) providing position indicating means operable to determine a particular location on said disk upon which said polarized light impinges;
   G) providing a light collector displaced from said disk upon which said polarized light impinges, said light collector having
      i) an effective light receiving aperture having a width larger than width of said light beam so as to be operable to fully receive said beam, and
      ii) light intensity measuring means operative on received light;
   H) in a measurement, with respect to said particular location on said disk, directing said polarized light against said disk at said particular location and, during said measurement,
      i) reflecting said polarized light from said particular disk location, through said effective light receiving aperture of said light collector, and
      ii) measuring the amplitude of said received polarized light during said measurement; and
   I) determining at least one of wear of said coating layer and change in lubricant layer thickness at said particular disk location at least partially in response to said amplitude measurement.

3. A method of evaluating in at least one of lubricant coating thickness and coating wear on magnetic media disks subject to variable environmental and test conditions, such method comprising:

A) providing a magnetic media disk including
   i) a magnetic media layer,
   ii) a coating layer overlying said magnetic media layer, and
   iii) a lubricant layer overlying said coating layer;
B) supporting said magnetic media disk for rotation about a central axis extending normal to the substrate plane of said disk, and positioned for relative translation orthogonally of said axis with respect to a light source, said supporting being operable to selectively rotate said magnetic media disk about said axis as illumination is independently translated on said rotating disk orthogonally of said axis;
C) generating a collimated light beam with the light source displaced from said magnetic media disk;
D) controlling a cooler to maintain a generally constant temperature of said light source, and stabilizing said light source to
   i) maintain a constant intensity of light in said collimated light beam, and
   ii) maintain a constant wavelength of light in said collimated light beam;
E) polarizing said collimated light beam emanating from said temperature stabilized light source to selectively provide
   i) p-polarized light, and
   ii) s-polarized light;
F) providing position indicating means operable to determine a particular location on said disk upon which said polarized and collimated light beam impinges;
G) providing an integrating sphere displaced from said disk upon which said beam impinges, said integrating sphere having
   i) a light receiving aperture having an axis inclined relative to said plane of said disk and a width larger than the width of said light beam so as to be operable to fully receive said beam from diverse, radially displaced light beam impingement locations on said disk, said aperture being generally axially intersected by specularly reflected light from said disk, and
   ii) light intensity measuring means defined by at least a portion of the interior of said integrating sphere;
H) in a first measurement, and in respect to said particular location on said disk directing said polarized and collimated light beam against said disk at said particular location and, during said first measurement,
   i) reflecting said light beam from said particular disk location, through said light receiving aperture of said integrating sphere, and into the interior of said integrating sphere, and
   ii) independently measuring the amplitude of each of said p-polarized and said s-polarized light impinging upon the interior of said integrating sphere during said first measurement;
I) subsequent to a period of rotation of said disk and in a second measurement with respect to said particular location on said disk, directing said polarized and collimated light beam again against said disk at said particular location and, during said second measurement
   i) reflecting said light beam from said first disk location, through said light receiving aperture of said integrating sphere, and into the interior of an integrating sphere, and
   ii) independently measuring the amplitude of each of said p-polarized and said s-polarized light impinging upon the interior of said integrating sphere during said second measurement;
J) determining the difference in amplitude of each of said p-polarized and said s-polarized light increments impinging upon said interior of said integrating sphere during first and second measurements; and
K) determining at least one of wear of said coating layer and change in lubricant layer thickness at said particular disk location in response to at least one of
   i) a difference in amplitude between said first and second measurements, of said p-polarized light impinging upon said interior of said integrating sphere; and
   ii) a difference in amplitude between said first and second measurements, of said s-polarized light impinging upon the interior of said integrating sphere.

4. A method of evaluating in at least one of lubricant coating thickness and coating wear on magnetic media disks subject to variable environmental and test conditions, such method comprising:
A) providing a magnetic media disk including
   i) a magnetic media layer,
   ii) a coating layer overlying said magnetic media layer, and
   iii) a lubricant layer overlying said coating layer;
B) supporting said magnetic media disk for rotation about a central axis extending normal to the substrate plane of said disk, and positioned for relative translation orthogonally of said axis with respect to a light source, said supporting being operable to selectively rotate said magnetic media disk about said axis as illumination is independently translated on said rotating disk orthogonally of said axis;
C) generating a collimated light beam with the light source displaced from said magnetic media disk;
D) maintaining a generally constant temperature of said light source and stabilizing said light source to
   i) maintain a constant intensity of light in said collimated light beam, and
   ii) maintain a constant wavelength of light in said collimated light beam;
E) polarizing said collimated light beam emanating from said temperature stabilized light source to provide polarized light;
F) providing position indicating means operable to determine a particular location on said disk upon which said polarized light impinges;
G) providing an integrating sphere displaced from said disk upon which said polarized light impinges, said integrating sphere having
   i) a light receiving aperture having an axis inclined relative to said plane of said disk and a width larger than the width of said light beam and operable to fully receive said beam from diverse, radially displaced light beam impingement locations on said disk, said aperture being generally axially intersected by the specular polarized light reflected from said disk, and
   ii) light intensity measuring means defined by at least a portion of the interior of said integrating sphere;
H) in a measurement, with respect to said particular location on said disk, directing said polarized light against said disk at said particular location and, during said measurement, i) reflecting said polarized light from said particular disk location, through said light receiving aperture of said integrating sphere, and into the interior of said integrating sphere, and ii) measuring the amplitude of said polarized light impinging upon the interior of said integrating sphere during said measurement; and I) determining at least one of wear of said coating layer and change in lubricant layer thickness at said particular disk location at least partially in response to said amplitude measurement.

5. A method according to claim 4, wherein the step of supporting includes supporting on a turntable with an encoder to specify angular position, and the step of providing position indicating means includes providing a controllably translatable assembly for moving said light beam across the disk such that angular position data of said turntable and radial position data of said translatable assembly identify an illuminated position on the disk.

6. A method according to claim 5, further wherein the step of measuring includes compiling a data set synchronized with said angular and radial position data of values of light reflected from said disk at a plurality of spots substantially covering at least a region of the disk.

7. A method according to claim 6, wherein the plurality of spots lie on a spiral and cover only a portion of the disk.

8. A method according to claim 6, wherein the spots lie on a plurality of parallel circumferential tracks.

9. A method according to claim 8, wherein the spots each have a dimension under approximately ten micrometers and collectively cover substantially the entire surface of the disk.

10. A method according to claim 9, wherein the step of providing a controllably translatable assembly includes providing a substantially rigid carriage directing the light source and the aperture of said sphere at a common point, so that the light receiving aperture collects light specularly reflected from the common point as motion of the carriage radially translates the common point across the disk.

11. A method according to claim 6, further comprising the step of locating said turntable and translatable assembly in an environmental chamber to subject the disk to a controlled environmental condition prior to performing a measurement.

12. Apparatus for evaluating at least one of lubricant coating thickness and coating wear on a magnetic media disk subject to variable environmental and test conditions, the magnetic media disk including i) a magnetic media layer, ii) a coating layer overlying said magnetic media layer, and iii) a lubricant layer overlying said coating layer, and such apparatus comprising:

means for supporting said magnetic media disk for rotation about a central axis extending normal to the substrate plane of said disk, and positioned for relative translation orthogonally of said axis with respect to a light source, said means for supporting being operable to selectively rotate said magnetic media disk about said axis as illumination is independently translated on said rotating disk orthogonally of said axis;

means for generating a collimated light beam with the light source displaced from said magnetic media disk;

means for polarizing said collimated light beam emanating from said light source to provide polarized light;

position indicating means for determining a particular location on said disk upon which said polarized light impinges;

an integrating sphere displaced from said disk upon which said polarized light impinges, said integrating sphere having i) a light receiving aperture having an axis inclined relative to said plane of said disk and a width larger than width of said light beam so as to be operable to fully receive said beam from diverse, radially displaced light beam impingement locations on said disk, said aperture being generally axially intersected by the specular polarized light reflected from said disk, and ii) light intensity measuring means defined by at least a portion of the interior of said integrating sphere;

means for determining a measurement with respect to said particular location on said disk by directing said polarized light against said disk at said particular location and, during said measurement, i) reflecting said polarized light from said particular disk location, through said light receiving aperture of said integrating sphere, and into the interior of said integrating sphere, and ii) measuring the amplitude of said polarized light impinging upon the interior of said integrating sphere during said measurement, said means for determining compiling a map of disk locations and detected amplitudes over said disk, said map determining at least one of wear of said coating layer and change in lubricant layer thickness at said particular disk location at least partially in response to said amplitude measurement.

13. Apparatus for evaluating at least one of lubricant coating thickness and coating wear on a magnetic media disk subject to variable environmental and test conditions, the magnetic media disk including i) a magnetic media layer, ii) a coating layer overlying said magnetic media layer, and iii) a lubricant layer overlying said coating layer; wherein the apparatus comprises means for supporting said magnetic media disk for rotation about a central axis extending normal to the substrate plane of said disk, and positioned for relative translation orthogonally of said axis with respect to a light source, said supporting means being operable to selectively rotate said magnetic media disk about said axis as illumination is independently translated on said rotating disk orthogonally of said axis;

means for generating a collimated light beam with the light source displaced from said magnetic media disk;

means for sensing temperature and modifying the temperature of said light source to maintain a generally constant temperature thereof and, operating at said generally constant temperature, means for stabilizing driving of said light source to i) maintain a constant intensity of light in said collimated light beam; and ii) maintain a constant wavelength of light in said collimated light beam;

means for polarizing said collimated light beam emanating from said temperature stabilized light source to provide polarized light;

position indicating means operable to determine a particular location on said disk upon which said polarized light impinges;

a light collector displaced from said disk upon which said polarized light impinges, said light collector having i) an effective light receiving aperture having a width larger than width of said light beam so as to be operable to fully receive said beam, and ii) light intensity measuring means operative on received light;

means for determining a measurement, with respect to said particular location on said disk by directing said polarized light against said disk at said particular location and, during said measurement,
  i) reflecting said polarized light from said particular disk location, through said effective light receiving aperture of said light collector, and
  ii) measuring the amplitude of said received polarized light during said measurement; said means for determining compiling a map of disk locations and detected amplitudes over said disk for determining at least one of wear of said coating layer and change in lubricant layer thickness at particular disk locations at least partially in response to said amplitude measurement.

14. Apparatus according to claim 13, wherein the means for supporting includes a turntable with an encoder to specify angular position, and the position indicating means includes a controllably translatable assembly for moving said light beam across the disk such that angular position data of said turntable and radial position data of said translatable assembly identify an illuminated position on the disk.

15. Apparatus according to claim 14, further wherein the means for determining a measurement compiles a data set synchronized with said angular and radial position data of values of light reflected from said disk at a plurality of spots substantially covering at least a region of the disk.

16. Apparatus according to claim 15, wherein the plurality of spots lie on a spiral and cover only a portion of the disk.

17. Apparatus according to claim 15, wherein the spots lie on a plurality of parallel circumferential tracks.

18. Apparatus according to claim 15, wherein the spots each have a dimension under approximately ten micrometers and collectively cover substantially the entire surface of the disk.

19. Apparatus according to claim 14, wherein the controllably translatable assembly includes a substantially rigid carriage orienting the light beam and the aperture of said sphere at a common point, so that the effective light receiving aperture collects light specularly reflected from the common point as motion of the carriage radially translates the common point across the disk.

20. Apparatus according to claim 13, further comprising an environmental chamber surrounding said turntable and translatable assembly for subjecting the disk to controlled environmental conditions prior to performing a measurement.

* * * * *